United States Patent [19]

Kawakami et al.

[11] 4,146,551

[45] Mar. 27, 1979

[54] PROCESS FOR PRODUCING MAGNESIUM SALT OF SULFONIC ACID AND SULFURIC ESTER

[75] Inventors: Akira Kawakami, Sakura; Yoshio Aoki, Tokyo, both of Japan

[73] Assignee: The Lion Fat and Oil Co., Ltd., Tokyo, Japan

[21] Appl. No.: 898,794

[22] Filed: Apr. 24, 1978

[30] Foreign Application Priority Data

Apr. 28, 1977 [JP] Japan .................................. 52/48403

[51] Int. Cl.$^2$ ................. C07C 143/16; C07C 143/26; C07C 141/04; C07C 141/08
[52] U.S. Cl. ........................... 260/458 R; 260/459 R; 260/505 N; 260/513 R
[58] Field of Search ........... 260/505 N, 459 R, 513 R, 260/458 R

[56] References Cited

U.S. PATENT DOCUMENTS 2,616,911  11/1952  Asseff et al. ..................... 260/505 N Primary Examiner—Nicky Chan
Attorney, Agent, or Firm—Armstrong, Nikaido, Marmelstein & Kubovcik

[57] ABSTRACT

Disclosed is a process for producing the magnesium salt of sulfonic acids and sulfuric esters comprising the step of neutralizing the sulfonic acids and sulfuric esters with an aqueous dispersion containing: (1) at least one neutralizing agent selected from the group consisting of magnesium oxide and magnesium hydroxide, and; (2) at least one neutralizing accelerator selected from the group consisting of benzoic acid, citric acid, malic acid, phosphoric acid, polyphosphoric acid and water-soluble salts thereof under a pH of not more than approximately 6.

11 Claims, No Drawings

PROCESS FOR PRODUCING MAGNESIUM SALT OF SULFONIC ACID AND SULFURIC ESTER

BACKGROUND OF THE INVENTION

1. Field of the Invention

The present invention relates to a process for effectively producing the magnesium salt of sulfonic acids and sulfuric esters suitable for use as a surface-active agent.

2. Description of the Prior Art

The sodium salt of sulfonic acids and sulfuric esters has heretobefore been well-known as a surface-active agent. Recently, the magnesium salt of sulfonic acids and sulfuric esters has become of major interest as a surface-active agent having an excellent frothing property. The simplest known method for producing the magnesium salt of sulfonic acids or sulfuric esters is a metathesis process or a double-decomposition process, in which the sodium salt of organic sulfonic acids or sulfuric esters is reacted with any water-soluble magnesium compound. However, this method is not recommendable due to the fact that large quantities of by-products are necessarily produced. On the other hand, methods in which organic sulfonic acids and sulfuric esters are neutralized with magnesium oxide or magnesium hydroxide are known. These methods have an advantage that no by-product is formed. However, these methods have a disadvantage that, since magnesium oxide and magnesium hydroxide to be used as a neutralizing agent are only slightly soluble in water, a long period neutralization operation is required.

SUMMARY OF THE INVENTION

The objects of the present invention are to obviate the above-mentioned disadvantages of the conventional manufacturing process for the magnesium salt of organic sulfonic acids and/or sulfuric esters and to provide a process for effectively producing the magnesium salt of organic sulfonic acids and/or sulfuric esters by using magnesium oxide or magnesium hydroxide.

In accordance with the present invention, there is provided a process for producing the magnesium salt of sulfonic acids and sulfuric esters comprising the step of neutralizing said sulfonic acids and sulfuric esters with an aqueous dispersion containing: (1) at least one neutralizing agent selected from the group consisting of magnesium oxide and magnesium hydroxide, and; (2) at least one neutralizing accelerator selected from the group consisting of benzoic acid, citric acid, malic acid, phosphoric acid, polyphosphoric acid and water-soluble salts thereof under a pH of not more than approximately 6.

DESCRIPTION OF THE PREFERRED EMBODIMENTS

The neutralization process of the present invention can apply to any organic sulfonic acids or sulfuric esters which are capable of forming a water-soluble or a readily water-soluble anionic surface-active agent in the form of magnesium salt. By the term "a readily water-soluble anionic surface-active agent" is meant that the agent easily dissolves in water in the presence of other surface-active agents.

Examples of such organic sulfonic acids include linear alkylbenzene sulfonic acids having an alkyl radical of 10 to 15 carbon atoms, such as decylbenzene sulfonic acids, undecylbenzene sulfonic acids, dodecylbenzene sulfonic acids, tridecylbenzen sulfonic acids, tetrabenzene sulfonic acids and mixtures thereof; alkenyl sulfonic acids having 8 to 22 carbon atoms, produced by the sulfonation of α-olefin, vinylidene type oxefin and internal olefin, such as $\Delta'$-dodecene sulfonic acid, $\Delta'$-tetradecene sulfonic acid, $\Delta'$-hexadecene sulfonic acid, $\Delta'$-octadecene sulfonic acid and their position isomers having a double bond in the different site and mixtures thereof; and hydroxy alkane sulfonic acids having 8 to 22 carbon atoms; produced by the hydrolysis of sultone containing the sulfonate of α-olefin and internal olefin, such as 3- and 4-hydroxydodecane sulfonic acids, 3- and 4-hydroxytetradecane sulfonic acids, 3- and 4-hydroxyoctadecane sulfonic acids and mixtures thereof; and the like.

The organic sulfuric esters used in the present invention include, for example, alkyl sulfuric esters having an alkyl radical of 8 to 22 carbon atoms, such as decyl sulfate, dodecyl sulfate (lauryl sulfate), tetradecyl sulfate (myristyl sulfate), hexadecyl sulfate, octadecyl sulfate and mixtures thereof, and the sulfuric esters of alcohols having $C_{11}$ to $C_{15}$ which are produced from olefins having $C_{10}$ to $C_{14}$, the sulfuric esters of alcohols having $C_{12}$ and $C_{13}$ which are produced from olefins having $C_{11}$ and $C_{12}$ and mixtures thereof and; alkyl ether sulfuric esters having an alkyl radicals of 8 to 22 carbon atoms and having an average addition mole number of alkylene oxide of 1 to 10, such as decyl triethoxy sulfate, dodecyl monoethoxy sulfate, dodecyl diethoxy sulfate, dodecyl triethoxy sulfate, dodecyl tetraethoxy sulfate, tetradecyl monoethoxy sulfate, tetradecyl diethoxy sulfate, tetradecyl triethoxy sulfate, tetradecyl tetraethoxy sulfate and mixtures thereof; sulfuric esters of alcohols having $C_9$ to $C_{11}$ (obtained from $C_8$-$C_{10}$ olefins) and having an average addition mol number of ethylene oxide of about 3, sulfuric esters of alcohols having $C_{11}$ to $C_{15}$ (obtaind from $C_{10}$-$C_{14}$ olefins) and having an average addition mol number of ethylene oxide of about 3 and mixtures thereof; and the like.

The aqueous dispersion containing a neutralizing agent and a neutralizing accelerator used in the practice of the present invention can be prepared either by dispersing the neutralizing agent in water followed by dissolving the neutralizing accelerator in the resulting dispersion or by dissolving the neutralizing accelerator in water followed by dispersing the neutralizing agent in the resulting aqueous solution.

The neutralizing agent, i.e. magnesium oxide and/or magnesium hydroxide can be dispersed in any amount in water. Although there is no critical content of the neutralizing agent in the aqueous dispersion, in order to ensure a good dispersion condition during the neutralization reaction, the content of the neutralizing agent in the aqueous dispersion is preferably within the range of from approximately 1.5 to approximately 15% by weight.

The neutralizing accelerator used in the practice of the present invention include benzoic acid, citric acid, malic acid and the water-soluble salt thereof (e.g. sodium benzoate, potassium benzoate, sodium citrate and sodium malate), and; phosphoric acid, polyphosphoric acid and the water-soluble salts thereof (e.g. sodium phosphate, sodium pyrophosphate, potassium pyrophosphate and sodium tripolyphosphate). The amount of the neutralizing accelerator dissolved in the aqueous dispersion is such that at least approximately 0.5% by weight of the dissolved neturalizing accelrator based on the total weight of the sulfonic acids and/or sulfuric esters to be neutralized is present during the neutralization reaction. However, since the neutralizing accelerator becomes an impurity in the resulting neutralizing reaction mixture, the amount of the neutralizing accelerator present in the aqueous dispersion during the neutralization reaction is preferably within the range of approximately 0.5 to approximately 10% by weight based on the total amount of the sulfonic acids and/or sulfuric esters to be neutralized, unless the presence of the neutralizing accelerator in the resulting neutralizing reaction mixture is not objectionable.

Generally, the neutralization reaction of the present invention can be carried out by adding organic sulfonic acids or sufluric esters to the aqueous dispersion placed in a reaction vessel. In addition it can be carried out by simultaneously charging the aqueous dispersion and the organic sulfonic acids or sulfuric esters into a reaction vessel. However, it is not recommendable that the aqueous dispersion be added to the organic sulfonic acids or sulfuric esters previously placed in a reaction vessel. This is because the agitation of the reaction mixture is difficult.

The neutralization reaction of the present invention is usually carried out at a pH of approximately 6 or less, and more preferably, at a pH of from 2 to 6. In the case where the pH of the reaction mixture is more than approximately 6, it is not preferable that the rate of the neutralization is very slow since the magnesium compounds used are only slightly soluble in the reaction mixture. Although no critical temperature of the neutralization reaction of the present invention exists, the neutralization reaction is generally carried out at a temperature of approximately 30 to approximately 70° C.

Under the above-mentioned reaction conditions, the reaction products containing 10 to 70% by weight of the magnesium salt of organic sulfonic acids or sulfuric esters can be obtained and can be directly utilized as an anionic surface-active agent for a cleaning agent (or a detergent).

As is clear from the above description, according to the present invention the production time of magnesium salt of organic sulfonic acids, or sulfuric esters can be decreased to a relatively short period of time, which is similar to the production time of sodium salt. It is believed that this is because the anion of the neutralizing accelerator used in the present invention accelerates the dissolving rate of the neutralizing agents of the present invention (i.e. magnesium oxide and/or magnesium hydroxide) into water, whereby the rate of the neutralization reaction is accelerated.

In order to further illustrate the present invention, the following specific examples are given. It is to be understood, however, that this is merely intended in an illustrative and not limitative sense. In the examples, all percents are by weight unless otherwise indicated.

EXAMPLES 1 to 9

An aqueous dispersion containing the neutralizing agent and the neutralizing accelerator listed in Table 1 below was charged into a 500 ml beaker, and thereafter, 200 g of linear alkylbenzene sulfonic acid, having an average molecular weight of 323, was added thereto at a constant speed. Thus, a neutralizing reaction was carried out at a pH of 4 to 5 and a temperature of 40° to 50° C.

The amount of the aqueous dispersion used in each experiment was such that the neutralizing agent contained in the aqueous dispersion was theoretically consumed by the linear alkylbenzene sulfonic acid added to the reaction flask. The length of time from the start of the addition of the linear alkylbenzene sulfonic acid until the presence of the neutralizing agent could not be observed by the naked eye, after the completion of the addition of the linear alkylbenzene sulfonic acid, was measured and taken as the required neutralization time. The results are shown in Table 1.

Table 1

| Example No. | 1[*1] | 2[*2] | 3 | 4 | 5 | 6 | 7 | 8 | 9 |
|---|---|---|---|---|---|---|---|---|---|
| Neutralizing Agent(g) | | | | | | | | | |
| Mg(OH)$_2$ | 18.9 | 9.5 | 18.9 | 18.9 | 18.9 | 18.9 | 18.9 | 18.9 | |
| MgO | | | | | | | | | 13.1 |
| Content of Neutralizing Agent(%) | 7.9 | 1.7 | 8.0 | 8.1 | 8.1 | 12.5 | 8.1 | 8.1 | 5.6 |
| Neutralizing Accelerator (g) | | | | | | | | | |
| Benzoic acid | | | 4.0 | | | | | | |
| Sodium benzoate | | | | 5.9 | | | | | |
| Citric acid | | | | | 5.9 | | | | |
| Malic acid | | | | | | | | | 5.9 |
| Sodium phosphate | | | | | | 5.9 | | | |
| pyrophosphoric acid | | | | | | | 5.9 | | |
| Sodium tripolyphosphate | | | | | | | | 5.9 | |
| Neutralization Time (min) | 50 | 41 | 8 | 6 | 9 | 5.5 | 4 | 8.5 | 5.5 |

[*1]Comparative Example
[*2]Comparative Example (In this example 100 g of linearalkylbenzene sulfonic acid having M.W. of 323 was used and a 1000 ml beaker was used.)

EXAMPLES 10 to 16

The neutralizing reactions were carried out in the same manner as in the previous Examples, except that 200 g of alkyl ether sulfuric ester having alkyl radicals of $C_{12}$ to $C_{13}$, an average addition mole number of 3 and an average molecular weight of 410, was used in lieu of the linear alkylbenzene sulfonic acid. In addition, in these experiments 79.1 g of ethanol were incorporated into the aqueous dispersion. The ethanol was used in order to decrease the viscosity of the system. The used amounts and contents of the neutralizing agent, the used amounts of the neutralizing accelerator and the determined neutralization time are shown in Table 2.

Table 2

| Example No. | 10* | 11 | 12 | 13 | 14 | 15 | 16 |
|---|---|---|---|---|---|---|---|
| Neutralizing Agent(g) | | | | | | | |
| Mg(OH)$_2$ | | 14.2 | 14.2 | 14.2 | 14.2 | 14.2 | 14.2 |

Table 2-continued

| Example No. | 10* | 11 | 12 | 13 | 14 | 15 | 16 |
|---|---|---|---|---|---|---|---|
| MgO | | | | | | | 9.8 |
| Content of Neutralizing Agent(%) | 12.0 | 12.9 | 12.9 | 13.1 | 13.1 | 12.9 | 8.2 |
| Neutralizing Accelerator(g) | | | | | | | |
| Benzoic acid | | 5.9 | | | | | 5.9 |
| Sodium benzoate | | | 5.9 | | | | |
| Citric acid | | | | 7.9 | | | |
| Sodium citrate | | | | | 7.9 | | |
| Malic acid | | | | | | 5.9 | |
| Neutralization Time(min) | 35 | 5 | 5 | 9 | 9 | 8 | 5 |

*Comparative Example

EXAMPLES 17 to 21

The neutralizing reactions were carried out in the same manner as in the previous Examples 1 to 9, except that a 1000 ml beaker was used and 200 g of alkyl sulfuric ester having alkyl radicals of $C_{12}$ to $C_{13}$ and having an average molecular weight of 266 was used. The used amounts and contents of the neutralizing agent, the used amount of the neutralizing accelerator and the determined neutralization time are shown in Table 3.

Table 3

| Example No. | 17* | 18 | 19 | 20 | 21 |
|---|---|---|---|---|---|
| Neutralizing Agent(g) | | | | | |
| Mg(OH)$_2$ | 21.9 | 21.9 | 21.9 | 21.9 | 21.9 |
| Content of Neutralizing Agent(%) | 4.8 | 4.8 | 4.8 | 4.8 | |
| Neutralizing Accelerator(g) | | | | | |
| Benzoic acid | | 5.9 | | | |
| Citric Acid | | | 5.9 | | |
| Sodium phosphate | | | | 5.9 | |
| Pyrophospate | | | | | 5.9 |
| Neutralization Time(min) | 40 | 6 | 6.5 | 6.5 | t |

*Comparative Example

As is clearly shown in Tables 1, 2 and 3, in the cases where the aqueous dispersion containing both the neutralizing agent and the neutralizing accelerator was used according to the present invention (i.e. in the Examples 3 to 9, 11 to 16 and 18 to 21), the organic sulfonic acid and sulfuric esters were converted into the corresponding magnesium salts for a remarkably short time compared to Examples 1, 2, 10 and 17, in which the aqueous dispersion containing only neutralizing agent was used.

What we claim is:

1. A process for producing the magnesium salt of sulfonic acids and sulfuric esters comprising the step of netralizing said sulfonic acids and sulfuric esters with an aqueous dispersion containing:
   (1) at least one neutralizing agent selected from the group consisting of magnesium oxide and magnesium hydroxide, and;
   (2) at least one neutralizing accelerator selected from the group consisting of benzoic acid, citric acid, malic acid, phosphoric acid, polyphosphoric acid and water-soluble salts thereof under a pH of not more than approximately 6.

2. The process as claimed in claim 1, wherein at least one sulfonic acid is neutralized.

3. The process as claimed in claim 2, wherein said sulfonic acid is selected from the group consisting of linear alkylbenzene sulfonic acids having an alkyl radical of 10 to 15 carbon atoms, alkenyl sulfonic acids having 8 to 22 carbon atoms and hydroxy alkane sulfonic acid having 8 to 22 carbon atoms.

4. The process as claimed in claim 1, wherein at least one sulfuric ester is neutralized.

5. The process as claimed in claim 4, wherein said sulfuric ester is selected from the group consisting of alkylsulfuric esters having an alkyl radical of 8 to 22 carbon atoms and alkyl ether sulfuric esters having an alkyl radicals of 8 to 22 carbon atoms and having an average addition mole number of alkylene oxide of 1 to 10.

6. The process as claimed in claim 1, wherein said neutralizing accelerator is selected from the group consisting of benzoic acid, citric acid, malic acid and water-soluble salts thereof.

7. The process as claimed in claim 1, wherein said neutralizing accelerator is selected from the group consisting of phosphoric acid, polyphosphoric acid and water-soluble salts thereof.

8. The process as claimed in claim 1, wherein said pH is within the range of from 2 to 6.

9. The process as claimed in claim 1, wherein said neutralization is conducted at a temperature within the range of from 30° to 70° C.

10. The process as claimed in claim 1, wherein the content of said neutralizing agent in the dispersion is within the range of from 1.5 to 15% by weight.

11. The process as claimed in claim 1, wherein the amount of said neutralizing accelerator is not less than 0.5% by weight, based on the total amount of the sulfonic acids and sulfuric esters.

* * * * *